United States Patent [19]

Guerrant et al.

[11] Patent Number: 5,561,111
[45] Date of Patent: Oct. 1, 1996

[54] STABLE GLUTAMINE DERIVATIVES FOR ORAL AND INTRAVENOUS REHYDRATION AND NUTRITION THERAPY

[75] Inventors: Richard L. Guerrant; Timothy L. MacDonald, both of Charlottesville, Va.; Aldo A. M. Lima, Fortaleza, Brazil; Nathan M. Thielman; Thomas Miller, both of Charlottesville, Va.

[73] Assignee: The University of Virginia Patent Foundation, Charlottesville, Va.

[21] Appl. No.: 362,914

[22] Filed: Dec. 23, 1994

[51] Int. Cl.$^6$ ............................................ A61K 38/04
[52] U.S. Cl. ..................... 514/17; 514/2; 514/18; 514/19; 514/8; 426/656; 426/658
[58] Field of Search ................... 514/2, 18, 19, 514/17, 8, 569; 426/656, 658

[56] References Cited

U.S. PATENT DOCUMENTS

| | | | |
|---|---|---|---|
| 4,377,570 | 3/1983 | Durette et al. | 424/88 |
| 4,868,155 | 9/1989 | Durette et al. | 514/19 |
| 4,987,123 | 1/1991 | Masaki et al. | |
| 5,036,052 | 7/1991 | Ozeki et al. | 514/19 |

OTHER PUBLICATIONS

Furst et al.; Kidney Int., (1989) 36/Suppl. 27 (S287–S292).
Tenenhaus (AN 94331132 Medline).
Scheppach (AN 94314122 Medline).
Tamada (AN 93280822 Medline).
Hammarquist (AN 91053374 Medline).
Ziegler T R, Young L S, Benfell K, Scheltinga M, Hortons K, Bye R et al., Clinical and metabolic efficacy of glutamine--supplemented parenteral nutrition after bone marrow transplantation. Ann Intern Med 1992; 116:821–828.
Kandil H M, Chen W. Argenzio R A, Berschneider H M, Rhoads J M. L– glutamine metabolism stimulates ornithine Decarboxylase (ODC) activity and proliferation in a porcine jejunal enterocyte line. Gastroentrol 1993; 104(4), part 2:A627.

Hammarqvist F, Wernerman J, Ali R, von der Decken A, and Vinnars E. Addition of glutamine to total parenteral nutrition after elective abdominal surgery spares free glutamine in muscle, counteracts the fall in muscle protein synthesis, and improves nitrogen balance. Annals of Surgery 1989; 209:455–461.

Lima A A M, Soares A M, Freire Jr. J E, and Guerrant R L. Cotransport of sodium with glutamine, alanine and glucose in the isolated rabbit ileal mucosa. Braz J Med Biol Res 1991; 25:637–640.

Rhoads J M, Keku E O, Quinn J, Woosley J, Lecce J G. L-glutamine stimulates jejunal sodium and chloride absorption in pig rotavirus enteritis. Gastroenterol 1991; 100:683.

Punjabi N H, Kumala S, Rasidi C, et al. Glutamine supplemented ORS is superior to standard citrate glucose ORS for the maintenance therapy of adult cholera patients in Jakarta (Abstract #53). Am J Trop Med Hyg 1991; 45(suppl):114.

Souba, W.W., *Glutamine Physiology, Biochemistry and Nutrition in Critical Illness*, 1992. R. G. Landes Company (Distributed by CRC Press).

*Primary Examiner*—Michael P. Woodward
*Assistant Examiner*—Benet Prickril
*Attorney, Agent, or Firm*—Oblon, Spivak, McClelland, Maier & Neustadt, P.C.

[57] ABSTRACT

A method for the treatment of dehydration or nitrogen deficiency-based malnutrition is provided which involves administering to a patient in need thereof an effective amount of a compound selected from oligopeptides formed from the coupling of one or more amino acids with glutamine, the product of coupling glucose with glutamine, the product of coupling glucose and one or more amino acids with glutamine, or the product from acylating glutamine with a carboxylic acid having from 2 to 6 carbon atoms.

4 Claims, 2 Drawing Sheets

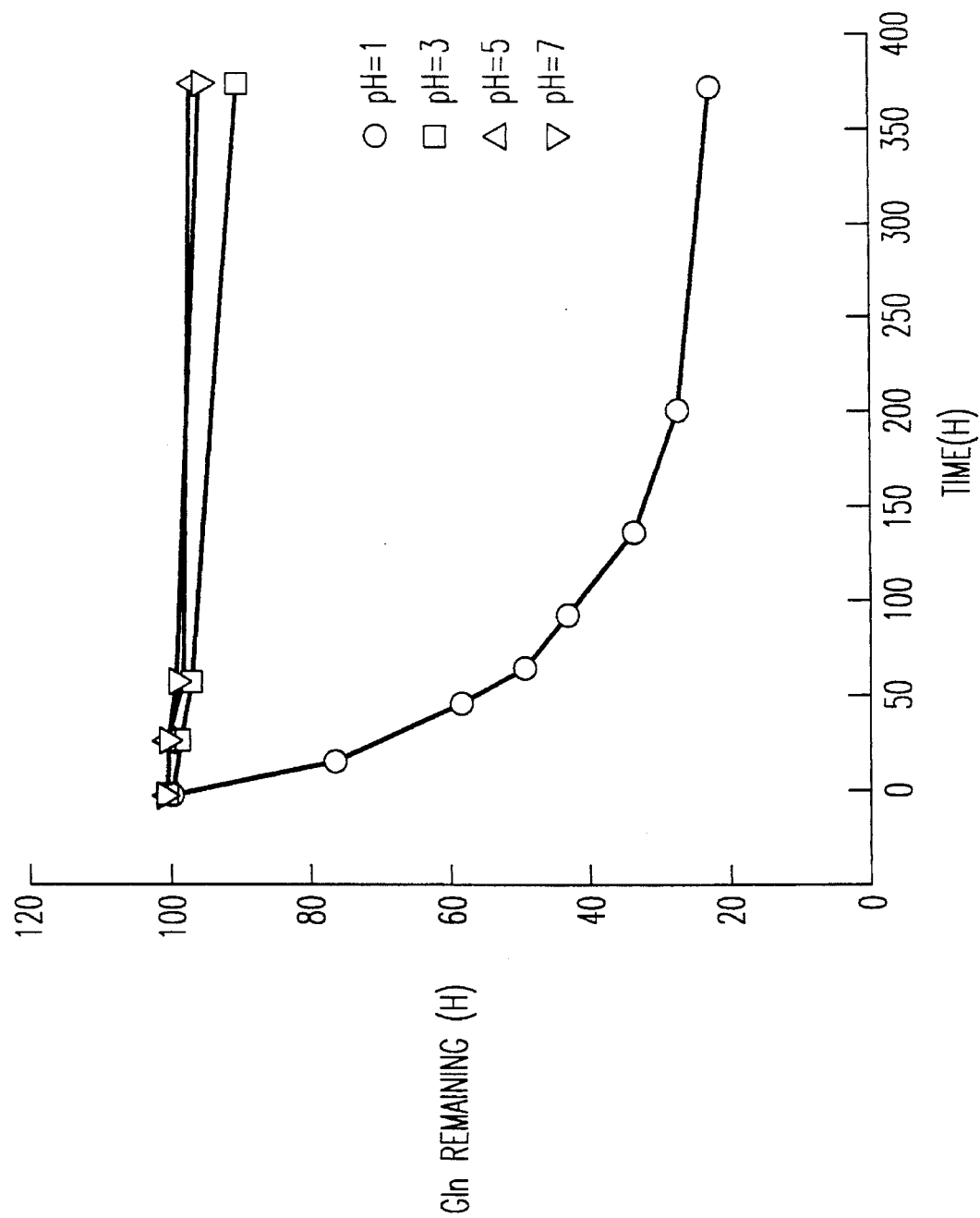

STABLE GLUTAMINE DERIVATIVES FOR ORAL AND INTRAVENOUS REHYDRATION AND NUTRITION THERAPY

BACKGROUND OF THE INVENTION

1. Field of the Invention

The present invention relates to stable glutamine derivatives and their use in rehydration and nutrition therapy.

2. Discussion of the Background

Glutamine, the chief metabolic fuel of the small intestine, is an amino acid which cotransports $Na^+$ across the enterocyte brush border membrane. It is known to be the major bowel nutrient and energy source and has been used in intravenous solutions to improve nitrogen balance, inhibit protein breakdown, stimulate the growth of epithelial cells, and reduce intestinal villous atrophy.

Additionally, various researchers have shown that glutamine stimulates the absorption of sodium and chloride and has been tried in oral rehydration solutions to reduce cholera diarrhea.

Viral enteritis is a leading cause of diarrhea in infants and toddlers less than 2 years old. Each year in the United States, about 22,000 infants are hospitalized for treatment of rotavirus-induced dehydration. Central to the pathophysiology of diarrhea in transmissible gastroenteritis (TGE), which is one experimental model of viral enteritis, are a number of intestinal abnormalities, including impaired glucose and amino acid-coupled $Na^+$ transport, defective NaCl absorption, diminished disaccharide hydrolysis, and reduced mucosal absorptive surface.

In a majority of cases, diarrheal disease morbidity and mortality is due to dehydration. The primary effect seen is the loss of fluid and electrolytes in diarrheal stools. An immediate effect in treatment of dehydration can be achieved by early oral administration of sugar (glucose) and electrolyte solution and continued feeding. However, conventional therapy by administration of oral rehydration formulations does not reduce stool volume or the duration of diarrhea. Thus, modifications of the oral rehydration therapy are needed to actually reduce stool volume or speed the recovery of normal mucosal function, which in turn would substantially enhance the acceptability and effectiveness of such therapy.

The physiological principle of oral rehydration therapy was first observed by Schultz and Curran (*Physiology Review,* 50:637–718 (1970)). They demonstrated the intestinal cotransport of sodium with glucose. Others have demonstrated the active transport of organic compounds by the small intestine which, when coupled with sodium absorption, enhances the absorption of water and other salts. (See Lima et al, *Bailliere's Clinical Tropical Medicine and Communicable Diseases,* 3:627–636 (1988) and Soares et al, *Brazilian Journal of Medical and Biological Research,* 24:111–113 (1991)).

The effects of organic compounds on salt and water absorption were first applied successfully to the treatment of patients with cholera and thereafter it was shown experimentally that the salt-substrate cotransport was substantially intact in cholera patients and that oral therapy with sodium, chloride, potassium, bicarbonate and glucose in the same solution could restore and maintain normal blood volume and electrolyte concentrations.

Organic molecules such as D-hexoses, neutral amino acids, dipeptides and tripeptides of neutral amino acids, and water-soluble vitamins can also enhance sodium absorption, followed by water absorption from the small intestine. The present inventors have previously shown the efficacy of glutamine in intestinal sodium absorption. (Lima et al, *Brazilian J. Med. Biol. Res.,* 25:637–640 (1992)). However, the greatest limitation to the oral use of glutamine is its instability and tendency to degrade in water and acid, conditions which are found in the stomach.

Bone marrow transplantation is being increasingly used in the treatment of hematologic malignancies. Patients undergoing bone marrow transplantation lose body protein because of the catabolic effects of chemotherapy, total body irradiation, and graft-versus-host disease. In addition, gastrointestinal toxicity often limits the consumption and absorption of enteral nutrients. Infectious complications also remain a major cause of morbidity in these patients. Infection accelerates protein loss, and protein-calorie malnutrition may decrease host resistance to microbial invasion.

Parenteral nutrition is known to attenuate such protein losses and may prevent complications associated with malnutrition. Despite routine use in many centers, parenteral nutrition is also, unfortunately, associated with an increased incidence of infection in patients receiving chemotherapy with or without irradiation, and also in those receiving allogeneic bone marrow transplantation. Further, despite conventional nutritional support, these patients still suffer from markedly negative nitrogen balance.

Modification of amino acid formulations may improve the clinical and metabolic efficacy of parenteral nutrition. Notably absent in all commercially available parenteral nutrient solutions is glutamine, because it has a shorter shelf-life than the commonly used amino acids and has been considered a nonessential amino acid. However, during catabolic states, glutamine concentrations in intracellular pools (primarily skeletal muscle) fall rapidly. This reduction in glutamine occurs due to use of glutamine for renal ammoniagenesis and as an oxidizable fuel for stimulated lymphocytes and macrophages and intestinal mucosal cells. Glutamine-enriched parenteral or enteral nutrition has been shown to enhance nitrogen balance, attenuate intestinal mucosal damage, decrease bacteremia, and improve survival after irradiation or chemotherapy when compared with glutamine-free nutrition. Limited clinical studies in postoperative patients have shown improved nitrogen retention with glutamine-enriched parenteral feeding. The clinical safety of L-glutamine added as a component of balanced parenteral nutrient solutions has recently been documented. (See Ziegler et al, *Annals of Internal Medicine,* 116:821–828 (1992) and references cited therein).

Masaki et al, U.S. Pat. No. 4,987,123, disclose the use of L-alanine, L-glutamine, L-alanyl-L-glutamine and salts thereof in the treatment of hepatic disorders. However, there is no indication as to the efficacy of using glutamine derivatives in treatment of disorders associated with dehydration or with nitrogen imbalance.

While the above-noted studies have shown the efficacy of Glutamine in rehydration and nutrition therapies, the instability of glutamine in the digestive tract has diminished its usefulness. Accordingly, there is needed a method for administration of glutamine to patients which will provide effective treatment in oral rehydration therapy and nutrition therapy, while overcoming the difficulties of instability in an acidic environment.

SUMMARY OF THE INVENTION

Accordingly, one object of this invention is to provide new stable glutamine derivatives capable of delivering glutamine to the body in oral or intravenous rehydration or nutrition therapy.

A further object of the present invention is to provide an improved method for treating conditions associated with dehydration or nitrogen deficiency based malnutrition using the stable glutamine derivatives of the present invention.

These and other objects of the present invention have been satisfied by the discovery that coupling glutamine with one or more additional amino acids, coupling glutamine with glucose, coupling glutamine with glucose and one or more additional amino acids, or acylating glutamine with a $C_2$–$C_6$ carboxylic acid provides a compound capable of surviving the digestive system of patients while at the same time delivering sufficient amounts of glutamine to the patient to obtain effective amounts in the patient's system to treat conditions associated with dehydration or malnutrition due to nitrogen loss.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 shows the pH dependent degradation of Glutamine under acidic conditions.

DESCRIPTION OF THE PREFERRED EMBODIMENTS

Figure 1:
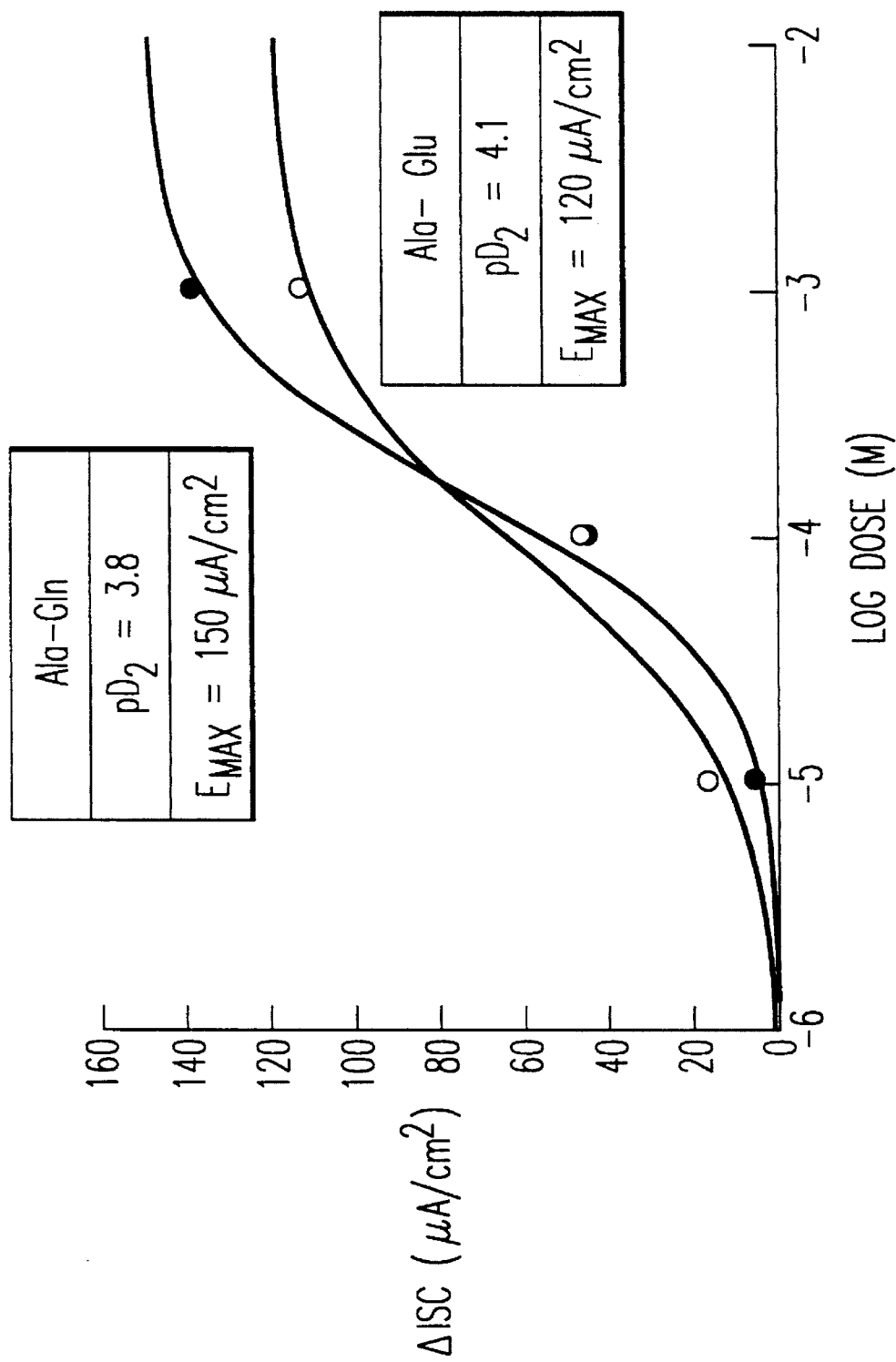
FIG. 1 is a graph showing the results obtained in intestinal sodium cotransport comparing the Ala-Gln compound of the present invention with Ala-Glu.

The present invention relates to new stable glutamine derivatives and their use in rehydration therapy a nutrition therapy.

The stable glutamine derivatives of the present invention can be prepared by coupling glutamine with one or more additional amino acids to provide oligopeptides, or with glucose, or both, or acylating glutamine with a carboxylic acid having 2 to 6 carbon atoms, to provide a compound which is stable to degradation under acidic environments. While any naturally occurring amino acid may be used as the additional amino acid coupled to the glutamine, it is preferred to use alanine or glutamine, alone or in combination as the additional amino acids. A preferred number of total amino acid groups present in the compounds used in the present method ranges from 2 to 5 (formed from coupling from 1 to 4 amino acids with glutamine), with dipeptides and tripeptides most preferred. Most preferred compounds include alanyl-glutamine, alanyl-glutaminyl glutamine and gamma-glutamyl glutamine. The compounds used in the present invention are known and can be prepared using conventional peptide coupling reactions, such as on a solid phase peptide synthesizer or using 1,3-diisopropyl-carbodiimide (DIPCDI) activation in solution coupling, as described in Hudson, *J. Org. Chem.*, 53(3):617–624 (1988) and Bodansky et al, *Synthesis*, pp. 453–463 (1991).

The compounds of the present invention have been shown to be much stabler in acidic water solutions (such as they would be expected to face in a patient's stomach or intestine) and to drive salt absorption comparable to if not better than glucose (see FIG. 1). FIG. 2 shows the pH dependent degradation of Glutamine under acidic conditions. By contrast, the acyl or alanyl derivatives of glutamine of the present invention were degraded <10% even at pH=1 over 360 hours at room temperature.

Since the ability to drive the intestinal sodium cotransport mechanism is known to directly correlate to efficacy in treatment of dehydration, especially when associated with diarrhea, these compounds provide an exciting approach to oral rehydration and nutrition therapy.

These compounds are useful not only in malnourished children with diarrhea, but also in patients kept too long on parenteral (IV) fluids or tube feedings or in those with damaged intestinal mucosa from infection or chemotherapy.

The present glutamine derivatives effectively block the degradation of glutamine in the highly acidic conditions which are encountered in the human stomach. In order to perform effectively in oral therapy, the compounds must be able to survive the conditions in the digestive tract while maintaining the ability to stimulate their absorption and maintain the integrity of the intestinal mucosa.

The glutamine derivatives of the present invention have been found to provide the requisite acid stability. Additionally, these glutamine derivatives provide intestinal sodium cotransport which is comparable to or higher than the use of glutamine itself.

The glutamine derivatives of the present invention can be administered either orally or intravenously.

When administered orally, the compounds can be administered as a liquid solution, powder, tablet, capsule or lozenge. The compounds can be used in combination with one or more conventional pharmaceutical additive or excipients used in the preparation of tablets, capsules, lozenges and other orally administrable forms.

When administered as an intravenous solution, the derivatives of the present invention can be admixed with conventional IV solutions containing various amino acids and nutrients, such as conventional parenteral therapy solutions. Such IV solutions are known in the art and used in rehydration and nutrition therapy.

The compounds of the present invention are administered at a dose range effective to bring about improved intestinal sodium cotransport.

A preferred dosage range of glutamine equivalent (Gln has a molecular weight of 146) is 0.05 to 0.8 g/kg/day of patient body weight, with approximately 0.5 to 0.6 g/kg/day or solutions of approximately 13 g/L glutamine equivalent (the solutions have sufficient glutamine derivative to provide an effective glutamine level equivalent to a solution of 13 g/L glutamine) or 1–10 mM glutamine derivatives being most preferred.

Conventional therapy regimens are followed in oral or intravenous rehydration or nutrition therapy of patients in need thereof. Such patients include children who are malnourished and suffer from diarrhea, patients kept too long on IV fluids or tube feeding, or those having damaged intestinal mucosa from infection or chemotherapy. The need for starting treatment in rehydration or nutrition therapy is judged by conventional standards. The therapy is continued until the patient has improved beyond the minimum hydration requirements or as long as the increased nutritional demands require.

Having generally described this invention, a further understanding can be obtained by reference to certain specific examples which are provided herein for purposes of illustration only and are not intended to be limiting unless otherwise specified.

EXAMPLES

To study intestinal sodium cotransport using the compounds of the present invention, Ala-Glu and Ala-Gln were tested according to the method of Lima et al, *Brazilian J. Med Biol. Res.*, 25:637–640 (1992) for measuring intestinal sodium cotransport in rabbit ileal mucosa mounted in Ussing chambers.

FIG. 1 shows the response in intestinal sodium cotransport using Ala-Gln and Ala-Glu in rabbit ileal mucosa. As shown the dose response increases dramatically in a non-linear fashion. Ala-Gln showed a maximum increase ($E_{max}$) in Isc of 150 µA/cm$^2$, with a pD$_2$ of 3.8. The pD$_2$ value is related to the ED$_{50}$ in accordance with the following formula:

$$-\log ED_{50} = pD_2.$$

Meanwhile, Ala-Glu showed an $E_{max}$=120 µA/cm$^2$, with a pD$_2$ of 4.1. Thus, the Ala-Gln compound of the present invention was found to provide comparable or improved intestinal sodium cotransport compared to Ala-Glu.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for oral rehydration and nutrition therapy comprising orally administering to a patient in need thereof an effective amount of a compound selected from the group consisting of oligopeptides having from 2 to 5 amino acid units and containing therein the amino acid sequence alanine-glutamine.

2. The method of claim 1, wherein said compound is selected from the group consisting of alanyl-glutamine, and alanyl-glutaminyl glutamine.

3. The method of claim 1, wherein said compound is administered in a dosage range of from 0.05 to 1.0 g/kg of said subjects body weight per day.

4. The method of claim 1, wherein said administering step is performed orally in the form of a liquid solution, liquid emulsion, powder, tablet, lozenge or capsule.

* * * * *

UNITED STATES PATENT AND TRADEMARK OFFICE
CERTIFICATE OF CORRECTION

PATENT NO.    : 5,561,111
DATED         : October 1, 1996
INVENTOR(S)   : Richard L. Guerrant et al.

It is certified that error appears in the above-identified patent and that said Letters Patent is hereby corrected as shown below:

Column 1,
Line 5, please insert -- GOVERNMENT SUPPORT
This invention was made with government support under Grant No. T32 AI007046 awarded by the National Institutes of Health. The government has certain rights in the invention. --

Signed and Sealed this

Second Day of August, 2005

JON W. DUDAS
*Director of the United States Patent and Trademark Office*